United States Patent
Tomita et al.

(10) Patent No.: US 7,037,377 B2
(45) Date of Patent: May 2, 2006

(54) PROCESS FOR PRODUCING LACTUROSE-CONTAINING POWDER COMPOSITION, LACTUROSE-CONTAINING POWDER COMPOSITION OBTAINED BY THE PROCESS AND FEED ADDITIVE

(75) Inventors: Mamoru Tomita, Zushi (JP); Sadayuki Kokubo, Kamakura (JP); Teruhiko Mizota, Yokohama (JP); Nobuo Ichihashi, Isehara (JP); Nobuo Seki, Yamato (JP); Kenji Nishi, Zama (JP)

(73) Assignee: Morinaga Milk Industry Co., Ltd., (JP)

( * ) Notice: Subject to any disclaimer, the term of this patent is extended or adjusted under 35 U.S.C. 154(b) by 0 days.

(21) Appl. No.: 10/516,362

(22) PCT Filed: May 28, 2003

(86) PCT No.: PCT/JP03/06684

§ 371 (c)(1),
(2), (4) Date: Nov. 30, 2004

(87) PCT Pub. No.: WO03/101218

PCT Pub. Date: Dec. 11, 2003

(65) Prior Publication Data

US 2005/0166911 A1    Aug. 4, 2005

(30) Foreign Application Priority Data

Jun. 4, 2002   (JP)   ............................. 2002-162774

(51) Int. Cl.
   C13F 3/00   (2006.01)
   C13D 3/16   (2006.01)
(52) U.S. Cl. ............................. 127/30; 127/55; 127/58
(58) Field of Classification Search ............ 127/30, 127/55, 58
   See application file for complete search history.

(56) References Cited

U.S. PATENT DOCUMENTS

| 4,057,655 A | 11/1977 | Okada et al. ............ 426/583 |
| 4,142,916 A | 3/1979 | Ogasa et al. ............ 127/63 |
| 5,026,430 A * | 6/1991 | de Haar et al. ............ 127/34 |
| 5,304,251 A | 4/1994 | Tomita et al. ............ 127/42 |

FOREIGN PATENT DOCUMENTS

| EP | 0 480 519 A1 | 4/1992 |
| EP | 0 532 173 A2 | 3/1993 |
| FR | 2 315 855 | 1/1977 |
| GB | 1 499 717 | 2/1978 |
| JP | 40-861 | 1/1940 |
| JP | 49-44332 | 11/1974 |
| JP | 54-15829 | 6/1979 |
| JP | 56-39200 | 4/1981 |
| JP | 5-43590 | 2/1993 |
| JP | 7-39318 | 2/1995 |
| JP | 2741812 | 1/1998 |
| WO | WO 00/36153 | 6/2000 |

OTHER PUBLICATIONS

Milk Science, *Multi-faceted Lactulose: Recent Research on its Development and Physiological Effects*, vol. 50, No. 2, pp. 39-47, 2001 (English Translation Attached), no month provided.

European Patent Office, *Supplementary European Search Report*, EP03733133, Dated Jun. 17, 2005 (3 Pages).

* cited by examiner

Primary Examiner—David Brunsman
(74) Attorney, Agent, or Firm—Wood, Herron & Evans, L.L.P.

(57) ABSTRACT

A lactulose-containing powder composition is produced by preparing a raw material liquid so that a lactulose content within a powder produced following spray drying is 10 to 50% by weight, a protein content is 0.2 to 9.0 parts by weight per 1 part by weight of lactulose, and a chlorine content is no more than 0.08 parts by weight per 1 part by weight of protein, and subsequently subjecting this raw material liquid to spray drying.

5 Claims, No Drawings

US 7,037,377 B2

PROCESS FOR PRODUCING LACTUROSE-CONTAINING POWDER COMPOSITION, LACTUROSE-CONTAINING POWDER COMPOSITION OBTAINED BY THE PROCESS AND FEED ADDITIVE

This application is a 371 of PCT/JP03/06684, filed 28 May 2003.

TECHNICAL FIELD

The present invention relates to a process for producing a lactulose-containing powder composition, as well as a lactulose-containing powder composition produced by such a process, and a feed additive.

BACKGROUND ART

Lactulose is well known as a growth factor for bifidobacterium, and its effectiveness in maintaining human health is well documented. Moreover, this effectiveness is not restricted to humans, but has also been demonstrated in animal feed, meaning its use is being investigated in a wide variety of fields.

The effectiveness of lactulose in humans has been reported, for example in "The many faces of lactulose: recent research trends in development and physiological effects" (Milk Science, Vol. 50, No. 2 (2001), pp. 39 to 47), which discloses information relating to the growth activity on bifidobacterium. Through this activity, lactulose provides a variety of effects, including improving the environment within the intestine, improving excretion, and accelerating defecation, meaning the positive effects on human health are well known.

In addition, the effectiveness of lactulose in the field of animal feed has also been reported in "Process for producing lactulose-containing powders for livestock feed" disclosed in Japanese Examined Patent Application, Second Publication No. S54-15829, and this application reports a number of effects for lactulose-containing powders, including weight gains in young pigs, and improved feed efficiency.

Furthermore, Japanese Unexamined Patent Application, First Publication No. H7-39318 discloses the effectiveness of lactulose as a feed for fish. This application discloses that feed comprising from 0.01 to 10% of one or more oligosaccharides selected from the group consisting of fructooligosaccharide, galactooligosaccharide, xylooligosaccharide, isomaltooligosaccharide, soybean oligosaccharide, gentiooligosaccharide, raffinose and lactulose promoted the growth of fish.

As described above, the effectiveness of lactulose is very apparent, and as its importance becomes more widely recognized, the number of fields in which lactulose is used continues to grow.

However, lactulose is difficult to crystallize or convert to powder form, and conventionally is usually used as an aqueous solution, although new powders, which improve the ease of use, are now beginning to be developed and used.

One example of a process for producing powdered lactulose is disclosed in Japanese Examined Patent Application, Second Publication No. S40-861, and involves producing a lactulose dried product by spray drying an aqueous solution containing a solid fraction comprising lactulose, lactose and other carbohydrates as required, wherein the maximum concentration of the solid fraction is from 45 to 50%, and the maximum lactulose content within the solid fraction is from 45 to 50%.

However, the lactulose-containing powder composition produced by this conventional process, although powdered, suffers from a number of handling problems at the point of use, including a high hygroscopicity, and absorption of moisture leading to adhesion to the container or solidification when used under high humidity environments such as during rainy weather. Furthermore, although a dried product with improved free-flow characteristics can be obtained by lowering the lactulose content within the solid fraction of the aqueous solution supplied to the spray drying process, this results in a reduction in the lactulose content within the product powder, meaning the product is economically less viable and therefore impractical.

As an alternative, Japanese Examined Patent Application, Second Publication No. S49-44332 (Japanese Patent (Granted) Publication No. 778,565) discloses a process for producing a powder with a high lactulose content of at least 55%, by spray drying a lactulose aqueous solution containing a protein as a drying assistant, in a quantity equivalent to at least 5% of the quantity of lactulose.

However, the lactulose-containing powder composition produced by this process also suffers from high hygroscopicity and poor stability with respect to high humidity levels.

On the other hand, Japanese Unexamined Patent Application, First Publication No. H5-43590 (Japanese Patent (Granted) Publication No. 2,848,721) discloses the production of a non-hygroscopic, high-purity crystalline lactulose by concentrating a lactulose syrup containing lactose and galactose and the like in addition to lactulose, cooling the resulting concentrated syrup, adding lactulose seed crystals and stirring to generate crystalline lactulose trihydrate, and then separating this lactulose trihydrate.

However, the purification and crystallization step in this production process for crystalline lactulose is complex, and if the processing of the mother liquor left after separation of the crystals is also considered, then the process is costly, resulting in an increase in the cost of the final product.

The present invention takes the above circumstances into consideration, with an object of providing a method for producing a lactulose-containing powder composition that enables the production, via a simple set of steps, of a lactulose-containing powder composition with a practical lactulose content and superior stability to humidity, as well as providing a lactulose-containing powder composition produced by such a process, and a feed additive that uses such a powder.

DISCLOSURE OF INVENTION

As a result of intensive investigation aimed at resolving the problems described above, the inventors of the present invention discovered that in order to produce a powdered product with a relatively high lactulose content, a process involving spray drying of a raw material liquid comprising lactulose and an added protein is preferred. They also discovered that in order to improve the stability to humidity, the important factors are the lactulose content in the powder following spray drying, and the quantity of negative chlorine ions, which are incorporated during the addition of the protein and the like and form the water-soluble salts that contribute to the hygroscopicity of the powder, and they were hence able to complete the present invention.

In other words, The method for producing a lactulose-containing powder composition according to the present invention comprises the steps of preparing a raw material liquid so that a lactulose content within the spray dried powder is 10 to 50% by weight, a protein content is 0.2 to 9.0 parts by weight per 1 part by weight of lactulose, and a chlorine content is no more than 0.08 parts by weight per 1 part by weight of protein, and then spray drying this raw material liquid.

Furthermore, the present invention also provides a lactulose-containing powder composition produced using the production process for a lactulose-containing powder composition according to the present invention.

In other words, the compositional makeup of a lactulose-containing powder composition according to the present invention comprises from 10 to 50% by weight of lactulose, from 0.2 to 9.0 parts by weight of protein per 1 part by weight of lactulose, and no more than 0.08 parts by weight per 1 part by weight of protein.

In addition, the present invention also provides a feed additive comprising a lactulose-containing powder composition of the present invention.

BEST MODE FOR CARRYING OUT THE INVENTION

As follows is a more detailed description of the present invention.

In the present invention, the lactulose can use either an aqueous solution or a commercially available lactulose powder. If a lactulose aqueous solution is used, then a conventional lactulose aqueous solution produced by isomerizing lactose and then conducting subsequent decolorization and purification steps can be used. Either a refined, high-purity lactulose aqueous solution, or a crude lactulose aqueous solution that still contains raw material components or other reaction products is suitable.

The protein used in the present invention can use proteins such as lactoprotein, casein, whey protein, and soybean protein. The protein may be a refined, high-purity product, a protein raw material that contains the above types of proteins, or a concentrated product in which the above proteins have been concentrated. If a solid protein is used, then the solid may be dissolved in water in advance to generate an aqueous solution.

To produce a lactulose-containing powder composition using the method of the present invention, a raw material liquid containing lactulose and protein is first prepared, and this raw material liquid is then spray dried to generate a powder. The spray drying can be conducted using conventional methods. If the water content in the powder produced following spray drying is too high then the storage stability deteriorates, whereas if the water content is too low, the quantity of impurities generated when the lactulose-containing powder composition is dissolved becomes excessively high, and there is also a risk of burning the powder during spray drying, and consequently the water content is preferably within a range from 2 to 5% by weight.

During spray drying of the raw material liquid, if the solid fraction within the raw material liquid is too high, the drying process becomes difficult, and adhesion to the inside of the spray drying apparatus increases. In contrast, if the solid fraction within the raw material liquid is too low, the powder becomes excessively fine, making recovery more difficult and increasing the drying costs. Accordingly, the solid fraction concentration within the raw material liquid is preferably set within a range from 30 to 50% by weight. Following preparation of the raw material liquid but prior to the spray drying, if required the raw material liquid may be subjected to sterilization and/or concentration using conventional methods.

To prepare the raw material liquid, lactulose, protein, and additional water as required, are mixed together and dissolved. In addition to lactulose and protein, the raw material liquid may also contain other added materials such as lactose, carbohydrates, fats, vitamins and minerals, provided their addition does not impair the drying characteristics during spray drying or the storage stability.

The raw material liquid is prepared so that a lactulose content within the powder produced following spray drying of the raw material liquid is 10 to 50% by weight, a protein content is 0.2 to 9.0 parts by weight per 1 part by weight of lactulose, and a chlorine content is no more than 0.08 parts by weight per 1 part by weight of protein.

Specifically, the absolute value of the water content varies from the raw material liquid prior to spray drying to that after spray drying, whereas the absolute value of the solid fraction does not vary, meaning the quantities (absolute quantities) of the lactulose, protein and chlorine do not change. As a result, if the water content in the powder following spray drying is be determined, the blend proportions of each of the materials that are required within the raw material liquid in order to achieve a spray dried powder of a desired composition can be calculated.

Particularly in the case of chlorine, increased chlorine content results in increased hygroscopicity, and consequently processes in which no active addition of chlorine is conducted, and the chlorine content is restricted to the quantity incorporated as part of the addition of the protein and other materials to the raw material liquid, are preferred. Accordingly, in order to control the chlorine content in the raw material liquid within the range described above, either proteins and other materials with chlorine content values that fall within the preferred range are selected, or the protein and/or other materials are subjected to a pretreatment such as ultrafiltration or electrodialysis to regulate the ratio between the protein and chlorine. For example, by conducting ultrafiltration, the protein content can be selectively increased, whereas by conducting electrodialysis, the chlorine content can be selectively reduced.

In this description, the lactulose content values refer to values obtained by measurements conducted in accordance with the "lactulose-containing food test method" disclosed in the health foods testing manual (edited by Japan Health Food and Nutrition Food Association, published Oct. 1, 1992).

Specifically, the measurement method described below is used.

(1) Reagents

Lactulose: Merck Corporation

Acetonitrile: for liquid chromatography (2) Equipment

High speed liquid chromatography (HPLC) apparatus with a differential refractometer detector Reduced pressure degasifier, data processing apparatus (3) Preparation of Test Solution Approximately 2 g of the sample is weighed accurately, made up to a constant 50 ml with water, and then allowed to filter naturally through filter paper. The filtrate is then filtered through an ultrafiltration membrane with a molecular weight cutoff of 10,000 to produce the test solution.

(4) Test Procedure (4-1) Qualitative Test

The above test solution and lactulose standard solutions are analyzed by HPLC under identical conditions, and the retention time on a chromatogram is identified.

(4-2) Quantitative Test

A. Basic Principles

Using HPLC, an absolute calibration curve method is conducted.

Lactulose standard solution and the test solution of identical volume are injected into the HPLC apparatus, and the quantity of lactulose is determined from the ratio of the area of the corresponding peak.

B. Examples of Analysis Conditions

Column: 4.6 mm (diameter)×250 mm, stainless steel pipe
Packing: Wakosil $5NH_2$ or equivalent product
Moving bed: acetonitrile:water=75:25 (v/v)
Flow rate: 1.0 m/min.
Detector: differential refractometer detector
Injection volume: 20 µl C. Calibration Curve Preparation Method Separate standard aqueous solutions containing 0.5 mg/ml, 1.0 mg/ml, 1.5 mg/ml, and 2.0 mg/ml respectively of a standard lactulose are prepared, and the lactulose peak area is measured under the analysis conditions described above, thereby enabling preparation of a calibration curve.

(5) Determination and Formulas (5-1) Qualitative Test

The above test solution and lactulose standard solutions are analyzed by HPLC under identical conditions, and the retention time on a chromatogram is identified.

(5-2) Quantitative Test

Using the lactulose peak area of the test solution on the chromatogram, the lactulose concentration is determined from the calibration curve, and the following formula is used to calculate the lactulose content within the sample.

Lactulose content (%) within product=5× (the lactulose concentration (mg/ml) determined from the calibration curve)/(sample quantity (g))

Furthermore, in this description the protein content values refer to values obtained by measurements conducted in accordance with the semimicro-Kjeldahl method, which represents the most common total nitrogen determination method. A specific example is the "quantitative analysis using a semimicro-Kjeldahl method" described on pages 163 to 165 of "Methods of Analysis in Health Science 2000" (edited by The Pharmaceutical Society of Japan, published by Kanehara & Co., Ltd., Feb. 29, 2000).

Specifically, the measurement method described below is used.

(1) Reagents (1-1) Decomposition Accelerator: $CuSO_4.5H_2O:K_2SO_4$ (1:4)

(1-2) 4% boric acid solution: 960 ml of water is added to 40 g of boric acid ($H_3BO_3$), the mixture is heated to dissolve the boric acid, and the solution is then cooled and made up to 1000 ml.

(1-3) Bromocresol green-methyl red indicator: 0.15 g of bromocresol green and 0.1 g of methyl red are dissolved in 180 ml of 99.5% ethanol, and water is then added to make the solution up to 200 ml.

(2) Apparatus

The apparatus for the semimicro-Kjeldahl method uses components of hardened glass, and the connections may use ground joints. The rubber used in the apparatus is boiled for 10 to 30 minutes in a 1 mol/l NaOH solution, subsequently boiled for 30 to 60 minutes in water, and then washed thoroughly in water prior to use.

(3) Test Procedure (3-1) Sample Decomposition

A quantity of the sample equivalent to a nitrogen content of 20 to 30 mg is weighed accurately, and then placed in a 250 to 300 ml Kjeldahl decomposition flask. 1 to 2 g of the decomposition accelerator and 20 to 30 ml of $H_2SO_4$ are added to the flask, and with the flask undergoing constant agitation, 1 ml of a 30% $H_2O_2$ solution is then added, and the flask is heated gently on a wire gauze. Once the sample has carbonized, the temperature is raised and the solution is boiled, and once the decomposition liquid has become a pale blue transparent solution, the solution is heated for a further 1 to 2 hours. The decomposition solution is then cooled, and approximately 100 ml of water is added gradually. The liquid is then transferred to a 200 ml measuring flask, and following cooling, water is added to bring the total volume up to 200.0 ml. 20.0 ml of this solution is then placed in a semimicro-Kjeldahl decomposition flask, and the decomposition flask is mounted in a distillation apparatus.

(3-2) Distillation: 15 ml of a 4% (w/v) boric acid solution and 3 drops of the bromocresol green-methyl red indicator are placed in the absorption flask of the distillation apparatus, a small quantity of water is added, and the tip of a cooler is placed in the liquid. 25 ml of a 30% (w/v) solution of NaOH is added from a dropping funnel of the distillation apparatus, a further 10 ml of water is washed into the flask, and steam is then immediately introduced from a steam generator, and distillation is distilled until the volume of distillate reaches 100 ml. The tip of the cooler is then lifted away from the surface of the liquid, and following the collection of a further few ml of distillate, the tip of the cooler is washed with a small quantity of water, which is subsequently combined with the flask contents.

(3-3) Titration: Using 5 mmol/l $H_2SO_4$, titration is conducted until the green color of the bromocresol green-methyl red indicator changes to a light gray red-purple color. A blank test is also conducted using the same method.

1 ml of 5 mmol/l $H_2SO_4$=0.14007 mg N (4) Calculations

N content (%) within sample=(0.14007×(a-b)×f× 200×100)/20× sample size (mg)

a: volume (ml) of 5 mmol/l $H_2SO_4$ solution required to neutralize the sample
b: volume (ml) of 5 mmol/l $H_2SO_4$ solution required to neutralize the blank
f: 5 mmol/l $H_2SO_4$ factor crude protein (%)=N (%)×nitrogen factor The value of the nitrogen factor varies depending on food materials, and is 6.38 in the case of milk and cheese.

Furthermore, in this description the chlorine content values refer to values obtained by measurements conducted in accordance with the silver nitrate titration method described on page 714 of the aforementioned "Methods of Analysis in Health Science 2000."

Specifically, the measurement method described below is used.

(1) Reagents (1-1) 0.01 mol/l NaCl solution: 0.5844 g of NaCl that has been heated to melting using a platinum dish is dissolved in water and the solution volume is made up to 1000 ml. 1 ml of a 0.01 mol/l NaCl solution corresponds with 0.3545 mg of Cl.

(1-2) 0.01 mol/l $AgNO_3$ solution: 1.7 g of $AgNO_3$ is dissolved in water and the solution volume is made up to 1000 ml. 1 ml of this solution is equivalent to 0.3545 mg of $Cl^-$. The factor for this solution is standardized using a 0.01 mol/l solution.

(1-3) $K_2CrO_4$ solution: 50 g of $K_2CrO_4$ is dissolved in a small quantity of water, and the 0.01 mol/l $AgNO_3$ solution is added until a light red precipitate forms. The precipitate is filtered off, and water is added to the filtrate to make the solution volume up to 1000 ml.

(1-4) $Al(OH)_3$: 10 g of aluminum potassium sulfate or aluminum ammonium sulfate is dissolved in 200 ml of water, and ammonia water is then added to precipitate $Al(OH)_3$. The supernatant liquid is poured off and discarded, water is added to the precipitate and mixed thoroughly, and following settling the supernatant liquid is again poured off and discarded. This operation is repeated several times, and the precipitate is then collected on filter paper, and washed thoroughly with water until reactions of $Cl^-$, $NH_4^+$ and $NO_2^-$ are no longer noticeable in the filtrate. This reagent is prepared fresh as required.

(2) Test Procedure 50 ml of the test solution is placed in a conical beaker or porcelain beaker, 0.5 ml of the $K_2CrO_4$ solution is added, and with the solution undergoing stirring with a glass rod, the 0.01 mol/l $AgNO_3$ solution is titrated until the test solution adopts a faint brown color that no longer disappears. The $Cl^-$ concentration is determined from the volume (ml) (a) of $AgNO_3$ solution added, using the following formula. The endpoint of the reaction is confirmed by placing another 50 ml of the test solution in an identical container, adding 0.5 ml of the $K_2CrO_4$ solution and comparing the colors of the two samples.

$$Cl^- (\mu g/ml) = 0.3545 a \times 1000 / \text{test solution (ml)}$$

If the volume of $AgNO_3$ solution required in the titration exceeds 25 ml, then another sample of the test solution is taken, from 0.2 to 0.3 ml of the $K_2CrO_4$ solution is added, and the above procedure is repeated.

If the $Cl^-$ value is extremely low, 100 to 200 ml of the test solution is placed in a conical flask, 0.2 to 0.3 ml of the $K_2CrO_4$ solution is added, the solution is evaporated to dryness using a water bath, the thus formed residue is dissolved in 2 to 3 ml of water, and the above procedure is then conducted.

If the coloring of the test solution is intense, then $Al(OH)_3$ is added to decolorize the solution, and the above procedure is then conducted.

In the present invention, if the lactulose content in the powder following spray drying, namely in the lactulose-containing powder composition of the present invention, is less than 10% by weight, the product is economically less viable and therefore impractical. Furthermore, in those cases where the lactulose-containing powder composition is then added to other nutritional compositions such as animal feed, if the lactulose content is too low, then the quantity of lactulose-containing powder composition that must be added to achieve the desired effects increases considerably, which can have an undesirable impact on the composition of the feed. In contrast, if the lactulose content of the lactulose-containing powder composition exceeds 50% by weight, then the stability to humidity becomes unsatisfactory.

If the protein content is less than 0.2 parts by weight per 1 part by weight of lactulose, then the stability to humidity becomes unsatisfactory. Furthermore, based on the fact that the lactulose-containing powder composition must contain at least 10% by weight of lactulose, the protein content within the powder composition cannot be any higher than 9 parts by weight per 1 part by weight of lactulose.

If the chlorine content exceeds 0.08 parts by weight per 1 part by weight of protein, the stability to humidity becomes unsatisfactory. There is no lower limit for the chlorine content, and smaller values are preferred.

According to the production process of the present invention, a lactulose-containing powder composition with a practical lactulose content of 10 to 50% by weight and superior stability to humidity can be produced via a simple set of steps.

Furthermore, a lactulose-containing powder composition produced in this manner comprises a practical lactulose content of 10 to 50% by weight, as well as improved hygroscopicity and favorable storage stability. Furthermore, because the composition has been powdered by spray drying, the lactulose is dispersed with good uniformity, meaning the composition is less prone to localized non-uniformity of the lactulose content than powdered mixtures produced by mixing different powdered ingredients together.

Moreover, because the composition contains lactulose as an active ingredient, a variety of favorable effects can be expected, including promotion of the growth of the beneficial bifidobacterium, favorable maintenance of health and prevention of infection by improving intestinal bacterial flora, and prevention of constipation by improving excretion.

Furthermore, the produced lactulose-containing powder composition is also effective as a feed additive for use within animal feed, including feed for both mammals and fish, and by blending this feed additive into such animal feed, a variety of favorable effects including promotion of the growth of the beneficial bifidobacterium, improved intestinal bacterial flora, improved excretion, and improved feed efficiency, and increased weight gain can be achieved with no loss in the stability of the feed relative to humidity.

In the following test examples and examples, unless otherwise stated the units "%" refer to "% by weight".

TEST EXAMPLE 1

Lactulose-containing powder compositions were produced so that the protein content per 1 part by weight of lactulose within the spray dried powder varied within a range from 0.1 to 0.4 parts by weight.

In other words, a commercially available lactulose aqueous solution (manufactured by Morinaga Milk Industry Co., Ltd., lactulose 52%, solid fraction 70%), a commercially available whey protein concentrate (manufactured by Milei GmbH, protein 76%, chlorine 0.05%, solid fraction 95%), and edible lactose (manufactured by Milei GmbH, lactose 95%, chlorine 0.02%, solid fraction 95%) were combined with water and dissolved, and once the solid fraction had been adjusted to 40%, the solution was sterilized by heating at 65° C. for 30 minutes to form a raw material liquid, which was subsequently spray dried using normal methods to yield a lactulose-containing powder composition. The heating conditions during spray drying included an intake temperature of 155° C. and an exhaust temperature of 85° C.

The respective blend quantities of the lactulose aqueous solution, the whey protein concentrate, and the edible lactose were varied during the production of the raw material liquid, enabling the preparation of nine different lactulose-containing powder compositions (sample numbers A-1 to A-9) with the compositions shown in Table 1. None of the samples displayed any particular problems during the powdering process.

In the following description, p/Lu refers to the protein content (units:parts by weight) per 1 part by weight of lactulose, and a/p refers to the chlorine content (units: parts by weight) per 1 part by weight of protein.

TABLE 1

| Sample number | Lactulose (%) (Lu) | Protein (%) (p) | Chlorine (%) (a) | Water content (%) | p/Lu | a/p |
|---|---|---|---|---|---|---|
| A-1 | 10 | 1.0 | 0.015 | 2.9 | 0.10 | 0.015 |
| A-2 | 10 | 2.1 | 0.016 | 3.0 | 0.21 | 0.008 |
| A-3 | 9.9 | 4.1 | 0.016 | 3.1 | 0.41 | 0.004 |
| A-4 | 30 | 3.1 | 0.011 | 2.9 | 0.10 | 0.004 |
| A-5 | 30 | 5.9 | 0.013 | 3.2 | 0.20 | 0.002 |
| A-6 | 30 | 12 | 0.016 | 3.2 | 0.40 | 0.001 |
| A-7 | 50 | 4.9 | 0.008 | 2.9 | 0.10 | 0.002 |
| A-8 | 50 | 10 | 0.010 | 3.1 | 0.20 | 0.001 |
| A-9 | 50 | 20 | 0.015 | 3.3 | 0.40 | 0.001 |

Subsequently, a 10 g sample of each of the lactulose-containing powder compositions was placed in a 100 ml beaker of diameter 50 mm, and left to stand at 25° C. in an environment of 81% relative humidity. After standing for 10 hours, each sample was inspected for external appearance, and was then sieved through a 16 mesh sieve (Tyler sieve, mesh size 0.991 mm), and the proportion of the powder that passed through the sieve relative to the total quantity of powder (the sieved ratio, units:%) was calculated. The results are shown in Table 2.

Samples for which the above 10 hours in a warm and humid environment caused no adhesion to the container or solidification as a result of moisture absorption can be used under normal conditions with no particular problems, either as a stand-alone composition or in a mixture.

TABLE 2

| Sample number | External appearance | Sieved ratio (%) |
|---|---|---|
| A-1 | Shrinkage and adhesion due to moisture absorption | 0 |
| A-2 | Good flowability | 95 |
| A-3 | Good flowability | 95 |
| A-4 | Shrinkage and adhesion due to moisture absorption | 0 |
| A-5 | Good flowability | 94 |
| A-6 | Good flowability | 95 |
| A-7 | Shrinkage and adhesion due to moisture absorption | 0 |
| A-8 | Soft lumps which readily break up | 93 |
| A-9 | Soft lumps which readily break up | 94 |

From the results shown in Table 1 and Table 2, it is clear that of the powders containing approximately 10% of lactulose (the samples A-1 to A-3), the sample with a protein content of 1% (p/Lu=0.10) absorbed moisture, displayed shrinkage and adhesion to the container, and would not pass through the sieve after 10 hours, whereas the samples in which the protein content was 2.1% (p/Lu=0.21) or greater displayed good stability to humidity and retained their powdered form.

Similarly, of the powders containing 30% of lactulose (the samples A-4 to A-6), the sample with a protein content of 3.1% (p/Lu=0.10) absorbed moisture and displayed shrinkage and adhesion to the container after 10 hours, whereas the samples in which the protein content was 5.9% (p/Lu=0.20) or greater displayed good stability to humidity.

Amongst the powders containing 50% of lactulose (the samples A-7 to A-9), the sample with a protein content of 4.9% (p/Lu=0.10) also absorbed moisture and displayed shrinkage and adhesion to the container, whereas in the samples in which the protein content was 10% (p/Lu=0.20) or greater, although the powders displayed some formation of soft lumps, these broke up readily meaning the sieved ratio was still high, indicating a satisfactory level of stability to humidity.

Accordingly, it is evident that in order to ensure favorable stability to humidity for a lactulose-containing powder composition, the quantity of protein must be at least 0.2 parts by weight per 1 part by weight of lactulose.

Similar results were achieved even when the type of protein was changed.

TEST EXAMPLE 2

Lactulose-containing powder compositions were produced so that the chlorine content per 1 part by weight of protein within the spray dried powder varied within a range from 0.002 to 0.14 parts by weight.

In this test example, the lactulose aqueous solution, edible lactose and water used the same materials as those described above in the test example 1. The whey was subjected to ultrafiltration, and four different whey powders and whey protein concentrates were prepared with varying ratios between the protein content and the chlorine content, and these protein sources were then used either singularly, or in combinations of two or more materials.

Using these ingredients, lactulose-containing powder compositions were produced using the same procedure as that described in the test example 1. By varying the blend quantities of the lactulose aqueous solution and the edible lactose, and varying the type and quantity of whey powder and/or whey concentrate used during the preparation of the raw material liquid, nine different lactulose-containing powder compositions (sample numbers B-1 to B-9) with the compositions shown in Table 3 were prepared. None of the samples displayed any particular problems during the powdering process.

A sample of each of the thus obtained lactulose-containing powder compositions was then left to stand for 10 hours in a similar manner to that described in the test example 1, and the external appearance and sieved ratio were then determined. The results are shown below in Table 4.

TABLE 3

| Sample number | Lactulose (%) (Lu) | Protein (%) (p) | Chlorine (%) (a) | Water content (%) | p/Lu | a/p |
|---|---|---|---|---|---|---|
| B-1 | 10 | 2.0 | 0.27 | 3.2 | 0.20 | 0.14 |
| B-2 | 10 | 2.0 | 0.16 | 3.1 | 0.20 | 0.080 |
| B-3 | 10 | 2.1 | 0.045 | 3.2 | 0.21 | 0.021 |
| B-4 | 10 | 2.0 | 0.020 | 3.1 | 0.20 | 0.010 |
| B-5 | 30 | 6.0 | 0.82 | 3.2 | 0.20 | 0.14 |
| B-6 | 30 | 6.1 | 0.49 | 3.2 | 0.20 | 0.080 |
| B-7 | 30 | 6.0 | 0.090 | 3.1 | 0.20 | 0.015 |
| B-8 | 30 | 6.2 | 0.020 | 3.1 | 0.21 | 0.003 |
| B-9 | 50 | 10 | 0.019 | 3.5 | 0.20 | 0.002 |

TABLE 4

| Sample number | External appearance | Sieved ratio (%) |
|---|---|---|
| B-1 | Shrinkage and adhesion due to moisture absorption | 0 |
| B-2 | Good flowability | 92 |
| B-3 | Good flowability | 94 |
| B-4 | Good flowability | 95 |
| B-5 | Shrinkage and adhesion due to moisture absorption | 0 |
| B-6 | Good flowability | 94 |
| B-7 | Good flowability | 95 |
| B-8 | Good flowability | 93 |
| B-9 | Good flowability | 95 |

From the results shown in Table 3 and Table 4, it is clear that although all of the powders have a substantially uniform protein content of approximately 0.2 parts by weight per 1 part by weight of lactulose (p/Lu), in the samples B-1 and B-5, where the chlorine content per 1 part by weight of protein (a/p) was significantly higher at 0.14 parts by weight, the powder displayed much higher hygroscopicity, and after standing for 10 hours had undergone significant undesirable change, having absorbed considerable moisture and hardened and adhered to the container.

In contrast, those powders in which the a/p ratio was no more than 0.08 parts by weight (the samples B-2 to B-4, and the samples B-6 to B-9) retained good flowability and displayed a favorable state even after standing for 10 hours.

Accordingly, it is evident that in order to ensure favorable stability to humidity for a lactulose-containing powder composition, the quantity of chlorine per 1 part by weight of protein (a/p) must be no more than 0.08 parts by weight.

Similar results were achieved even when the protein content relative to lactulose (p/Lu) was varied within a range from 0.2 to 9.0 parts by weight. In addition, similar results were also achieved even when the type of protein was changed.

TEST EXAMPLE 3

Lactulose-containing powder compositions were produced in which the lactulose content within the spray dried powders varied within a range from 5.1 to 55% by weight.

In other words, a commercially available lactulose-containing powder composition (manufactured by Morinaga Milk Industry Co., Ltd., lactulose 99%, solid fraction 99%), a whey protein concentrate prepared by ultrafiltration of whey (protein 29.3%, chlorine 0.45%, solid fraction 95%), and edible lactose (manufactured by Milei GmbH, lactose 95%, chlorine 0.3%, solid fraction 95%) and water were used, and were combined using the same procedure as the test example 1, to yield a series of lactulose-containing powder compositions (sample numbers C-1 to C-5) with the respective compositions shown in Table 5. None of the samples displayed any particular problems during the powdering process.

A sample of each of the thus obtained lactulose-containing powder compositions was then left to stand for 10 hours in a similar manner to that described in the test example 1, and the external appearance and sieved ratio were then determined. The results are shown below in Table 6.

COMPARATIVE TEST EXAMPLE 1

Lactulose-containing powder compositions were produced without the addition of any protein, using the spray drying method disclosed in Japanese Examined Patent Application, Second Publication No. S40-861.

In other words, a mixed solution comprising the same lactulose aqueous solution as that used in the test example 1 and the same edible lactose as that used in the test example 3 (lactulose 2%, lactose 33%, solid fraction 35%) was spray dried under conditions including an intake temperature of 155° C. and an exhaust temperature of 85° C., thus yielding the sample powder D-1 (lactulose content 5.1%) shown below in Table 5.

By altering the quantity of lactulose within the above mixed solution, a spray dried powder with a lactulose content of 10% (sample number D-2) and a spray dried powder with a lactulose content of 15% (sample number D-3) were also produced.

None of these samples displayed any particular problems during the powdering process.

A sample of each of the thus obtained powders was then left to stand for 10 hours in a similar manner to that described in the test example 1, and the external appearance and sieved ratio were then determined. The results are shown below in Table 6.

COMPARATIVE TEST EXAMPLE 2

A powder (sample number E-1) with the composition shown below in Table 5 was produced in accordance with the procedure disclosed in example 1 of Japanese Examined Patent Application, Second Publication No. S49-44332 (Japanese Patent (Granted) Publication No. 778,565).

In other words, a protein-containing solution prepared by mixing 298 g of acid casein (manufactured by NZMP, New Zealand Dairy Board, protein 84%), 18 g of potassium triphosphate, and 7.3 kg of water and then heating the mixture to achieve dissolution, was mixed with 10.0 kg of the same lactulose aqueous solution as that used above in the test example 1, and following adjustment of the pH to a value of 6.5, the solution was spray dried, yielding a powder (sample number E-1) with a lactulose content of 69%. The temperature conditions during spray drying included an intake temperature of 155° C. and an exhaust temperature of 85° C. The sample displayed no particular problems during the powdering process.

A sample of the thus obtained powder was left to stand for 10 hours in a similar manner to that described in the test example 1, and the external appearance and sieved ratio were then determined. The results are shown below in Table 6.

COMPARATIVE TEST EXAMPLE 3

A powder (sample number E-2) with the composition shown below in Table 5 was produced in accordance with the procedure disclosed in example 4 of Japanese Examined Patent Application, Second Publication No. S49-44332 (Japanese Patent (Granted) Publication No. 778,565).

In other words, a mixed solution was prepared by mixing 10.0 kg of the same lactulose aqueous solution as that used in the test example 1, 2.0 kg of whey powder (manufactured by Morinaga Milk Industry Co., Ltd., protein 12%), and 10.3 kg of water, and following adjustment of the pH to a value of 6.7, the solution was spray dried in the same manner as the comparative test example 2, yielding a powder (sample number E-2) with a lactulose content of 57%. The sample displayed no particular problems during the powdering process.

A sample of the thus obtained powder was left to stand for 10 hours in a similar manner to that described in the test example 1, and the external appearance and sieved ratio were then determined. The results are shown below in Table 6.

TABLE 5

| Sample number | Lactulose (%) (Lu) | Protein (%) (p) | Chlorine (%) (a) | Water content (%) | p/Lu | a/p |
|---|---|---|---|---|---|---|
| C-1 | 5.1 | 1.0 | 0.045 | 2.9 | 0.20 | 0.045 |
| C-2 | 10 | 2.1 | 0.057 | 3.0 | 0.21 | 0.027 |
| C-3 | 30 | 6.2 | 0.11 | 3.1 | 0.21 | 0.018 |
| C-4 | 50 | 10 | 0.16 | 2.9 | 0.20 | 0.016 |
| C-5 | 55 | 11 | 0.17 | 3.4 | 0.20 | 0.015 |
| D-1 | 5.1 | 0 | 0.031 | 2.8 | — | — |
| D-2 | 10 | 0 | 0.028 | 2.8 | — | — |
| D-3 | 15 | 0 | 0.026 | 3.0 | — | — |
| E-1 | 69 | 3.3 | 0 | 3.3 | 0.05 | 0 |
| E-2 | 57 | 2.6 | 0.038 | 3.2 | 0.05 | 0.015 |

TABLE 6

| Sample number | External appearance | Sieved ratio (%) |
|---|---|---|
| C-1 | Good flowability | 95 |
| C-2 | Good flowability | 93 |
| C-3 | Good flowability | 94 |
| C-4 | Soft lumps which readily break up | 94 |
| C-5 | Shrinkage and adhesion due to moisture absorption | 0 |
| D-1 | Good flowability | 94 |
| D-2 | Shrinkage and adhesion due to moisture absorption | 0 |
| D-3 | Shrinkage and adhesion due to moisture absorption | 0 |
| E-1 | Shrinkage and adhesion due to moisture absorption | 0 |
| E-2 | Shrinkage and adhesion due to moisture absorption | 0 |

From the results shown in Table 5 and Table 6, it is clear that of the lactulose-containing powder compositions C-1 to C-5 obtained in the test example 3, the compositions C-1 to C-4 in which the lactulose content was no more than 50% displayed favorable stability to humidity, whereas the composition C-5 with a lactulose content of 55% displayed unsatisfactory stability to humidity.

Furthermore, in the compositions D-1 to D-3 produced without the addition of protein, it was found that a favorable level of stability to humidity could be obtained if the lactulose content within the powder was reduced to 5.1%, but once the lactulose content reached 10% or greater, the powder became unstable relative to humidity.

In addition, favorable stability to humidity could not be achieved in either the composition E-2, in which the lactulose content within the powder was high at 57%, or the composition E-1, in which the lactulose content within the powder was high at 69% and the chlorine content was 0.

From these results it is evident that in order to ensure favorable stability to humidity, the upper limit for the lactulose content within a spray dried lactulose-containing powder composition is 50%.

Furthermore, in terms of a lower limit for the lactulose content within a lactulose-containing powder composition, in those cases where the lactulose-containing powder composition is used as an additive for combining with other nutritional compositions such as an animal feed product, the lactulose content is preferably at least 10% in order to ensure that the effects of the lactulose can be intensified without having any deleterious impact on the composition of the feed.

In the test example 3 and the comparative test examples 1 to 3 described above, similar results were achieved even when the protein content relative to each 1 part by weight of lactulose was varied within a range from 0.2 to 9.0 parts by weight, and the chlorine content relative to each 1 part by weight of protein was varied within a not exceeding 0.08 parts by weight. In addition, similar results were also achieved even when the type of protein was changed.

TEST EXAMPLE 4

This test example displays the effectiveness of a lactulose-containing powder composition according to the present invention as a feed additive.

In other words, 6.12 kg of the same lactulose aqueous solution as that used in the test example 1, 1.00 kg of the same whey protein concentrate (WPC) as that used in the test example 1, 4.55 kg of whey powder (WP) (manufactured by Morinaga Milk Industry Co., Ltd., protein 12%, chlorine 1.9%, solid fraction 96%), and water were blended together, and once the solid fraction had been adjusted to 40%, the solution was sterilized by heating at 65° C. for 30 minutes, and then spray dried in the same manner as the test example 1, thus yielding a lactulose-containing powder composition with a lactulose content of 30%, a protein content of 13%, a chlorine content of 0.86%, a p/Lu value of 0.43 parts by weight, and an a/p value of 0.066 parts by weight. The sample displayed no particular problems during the powdering process.

Fifteen LWD triple crossed female pigs at the weaning stage were subjected to a one week conditioning period using a commercially available weaning feed (Koromeal GS, manufactured by Nippon Formula Feed Manufacturing Co., Ltd.), and the pigs were then split into 3 groups with 5 pigs in each group. The first group continued with the above commercially available weaning feed, the second group were fed using the above commercially available weaning feed to which the additive described below had been added for the purposes of comparison, and the third group were fed using the above commercially available weaning feed containing 1.5% of the lactulose-containing powder composition produced above (equivalent lactulose content 0.45%), and each group was allowed to feed naturally for 2 weeks using ad libitum feeding. Drinking water was also freely available.

The additive used for the purposes of comparison in the feed of the second group was a mixture of WPC and WP in the same proportions as the lactulose-containing powder composition added to the feed of the third group, namely a mixture containing 0.15% WPC and 0.68% WP.

During the period of the test, no anomalies such as solidification or hardening of the feed were observed.

The weight of each animal was weighed at the start of the test and the completion of the test, and the weight increase (weight gain) was determined in each case. Furthermore, the quantity of residual feed was also measured at the completion of the test, the quantity of feed consumed was calculated, and the feed requirement ratio was calculated by dividing the quantity of feed consumed by the weight gain.

The results are shown below in Table 7. In Table 7, the test start weight, the test completion weight, the weight gain value, the feed consumption quantity, and the feed requirement ratio are each shown as a mean value and a range of deviation for each group. The statistical significance of the feed requirement ratio was determined by conducting multiple comparisons using the statistical analysis method known as the Tukey method for one-way layout analysis of variance, and then adjudging the result as statistically significant when the p value was less than 0.05 (the 5% significance level).

TABLE 7

| Test group | Test start weight (kg) | Test completion weight (kg) | Weight gain (kg) | Feed consumption (kg) | Feed requirement ratio |
|---|---|---|---|---|---|
| First group | 13.2 ± 2.3 | 18.4 ± 3.5 | 5.2 ± 1.1 | 11.6 ± 3.3 | 2.2 ± 0.2 |
| Second group | 13.1 ± 2.3 | 18.4 ± 3.3 | 5.3 ± 1.1 | 11.5 ± 2.9 | 2.2 ± 0.1 |
| Third group | 13.0 ± 2.2 | 19.3 ± 3.4 | 6.3 ± 1.3 | 12.0 ± 3.0 | 1.9 ± 0.1* |

*Significant relative to the groups without the * symbol ($p < 0.05$)

From the results in Table 7 it is clear that the third group, which used the feed containing added lactulose-containing powder composition according to the present invention, displayed a feed requirement ratio that was statistically significantly lower than that of the first and second groups, indicating a more favorable feed efficiency.

EXAMPLES

As follows is a description of examples according to the present invention.

Example 1

2.63 kg of sodium caseinate (manufactured by the New Zealand Dairy Board, protein 91%, chlorine 0.14%, solid fraction 95%) was mixed with, and dissolved in 11.3 kg of water, and this solution was then mixed with 10.2 kg of a lactulose aqueous solution (manufactured by Morinaga Milk Industry Co., Ltd., lactulose 49%, solid fraction 70%), and sterilized by maintaining at 80° C. for 10 minutes. Using a Niro atomizer (manufactured by Niro Inc.), the solution was then spray dried under conditions including an intake temperature of 155° C. and an exhaust temperature of 85° C., thus yielding 8.5 kg of a lactulose-containing powder composition. There were no particular problems during the spray drying process.

The thus obtained lactulose-containing powder composition contained 50% lactulose, 24% protein, and 0.04% chlorine, and had a water content of 3.1%, a protein content per 1 part by weight of lactulose of 0.5 parts by weight, and a chlorine content per 1 part by weight of protein of 0.001 parts by weight.

A 10 g sample of the thus produced lactulose-containing powder composition was placed in a 100 ml beaker of diameter 50 mm, and left to stand at 25° C. in an environment of 81% relative humidity. After standing for 10 hours, the sample was inspected for external appearance, and was then sieved through a 16 mesh sieve and the sieved ratio was calculated.

The results showed that after standing for 10 hours, some soft lumps had developed, although these were broken up by agitation, leaving the sample with good flowability. The sieved ratio was 94%, indicating a favorable level of stability to humidity.

Example 2

8.36 kg of a soybean isolated protein Fujipro WR (manufactured by Fuji Protein Technologies Inc., protein 91%, chlorine 0.18%, solid fraction 94%) was mixed with, and dissolved in 23.6 kg of water, and this solution was then mixed with 16.3 kg of the same lactulose aqueous solution as that used in the example 1, and following heating to 60° C., the solution was sterilized at 72° C. for 15 seconds. 24.1 kg of the sterilized solution was then spray dried in the same manner as the example 1, yielding 8.7 kg of a lactulose-containing powder composition. There were no particular problems during the spray drying process.

The thus obtained lactulose-containing powder composition contained 40% lactulose, 38% protein, and 0.08% chlorine, and had a water content of 3.3%, a protein content per 1 part by weight of lactulose of 1.0 parts by weight, and a chlorine content per 1 part by weight of protein of 0.002 parts by weight.

The stability to humidity of a 10 g sample of the thus produced lactulose-containing powder composition was assessed in the same manner as the example 1, and after standing for 10 hours, the sample had retained good flowability, and the sieved ratio was 94%, indicating a favorable level of stability to humidity.

Example 3

5.65 kg of a whey protein concentrate prepared from rennet whey (protein 35%, chlorine 0.94%, solid fraction 95%) was mixed with, and dissolved in 12.4 kg of water, and this solution was then mixed with 6.12 kg of the same lactulose aqueous solution as that used in the example 1, and the solution was sterilized by maintaining at 65° C. for 30 minutes. The sterilized solution was then spray dried in the same manner as the example 1, yielding 8.5 kg of a lactulose-containing powder composition. There were no particular problems during the spray drying process.

The thus obtained lactulose-containing powder composition contained 30% lactulose, 20% protein, and 0.53% chlorine, and had a water content of 3.3%, a protein content per 1 part by weight of lactulose of 0.7 parts by weight, and a chlorine content per 1 part by weight of protein of 0.03 parts by weight.

The stability to humidity of a 10 g sample of the thus produced lactulose-containing powder composition was assessed in the same manner as the example 1, and after standing for 10 hours, the sample had retained good flowability, and the sieved ratio was 95%, indicating a favorable level of stability to humidity.

Example 4

7.06 kg of skim milk powder (manufactured by Morinaga Milk Industry Co., Ltd., protein 34%, chlorine 1.3%, solid fraction 96%) was mixed with, and dissolved in 13.0 kg of water, and this solution was then mixed with 4.08 kg of the same lactulose aqueous solution as that used in the example 1, and the solution was then sterilized by heating to 80° C. and maintaining that temperature for 10 minutes. The sterilized solution was then spray dried in the same manner as the example 1, yielding 8.5 kg of a lactulose-containing powder composition. There were no particular problems during the spray drying process.

The thus obtained lactulose-containing powder composition contained 20% lactulose, 24% protein, and 0.88% chlorine, and had a water content of 2.9%, a protein content per 1 part by weight of lactulose of 1.2 parts by weight, and a chlorine content per 1 part by weight of protein of 0.04 parts by weight.

The stability to humidity of a 10 g sample of the thus produced powder was assessed in the same manner as the example 1, and after standing for 10 hours, the sample had retained good flowability, and the sieved ratio was 94%, indicating a favorable level of stability to humidity.

Example 5

1.34 kg of a whey protein concentrate (manufactured by Milei GmbH, protein 76%, chlorine 0.05%, solid fraction 95%), and 6.9 kg of a whey powder (manufactured by Morinaga Milk Industry Co., Ltd., protein 12%, chlorine 1.9%, solid fraction 96%) were mixed with, and dissolved in 13.4 kg of water, and this solution was then mixed with 2.5 kg of a lactulose aqueous solution (lactulose 40%, solid fraction 70%), and subsequently sterilized by maintaining at 63° C. for 30 minutes. The sterilized solution was then spray dried in the same manner as the example 1, yielding 8.7 kg of a lactulose-containing powder composition. There were no particular problems during the spray drying process.

The thus obtained lactulose-containing powder composition contained 10% lactulose, 18% protein, and 1.3% chlorine, and had a water content of 3.3%, a protein content per 1 part by weight of lactulose of 1.8 parts by weight, and a chlorine content per 1 part by weight of protein of 0.07 parts by weight.

The stability to humidity of a 10 g sample of the thus produced lactulose-containing powder composition was assessed in the same manner as the example 1, and after standing for 10 hours, the sample had retained good flowability, and the sieved ratio was 93%, indicating a favorable level of stability to humidity.

INDUSTRIAL APPLICABILITY

According to the present invention, a lactulose-containing powder composition with a practical lactulose content and superior stability to humidity can be produced via a simple set of steps.

The invention claimed is:

1. A method for producing a lactulose-containing powder composition, comprising the steps of:
   preparing a raw material liquid so that a lactulose content within a powder produced following spray drying is 10 to 50% by weight, a protein content is 0.2 to 9.0 parts by weight per 1 part by weight of lactulose, and a chlorine content is no more than 0.08 parts by weight per 1 part by weight of protein, and
   spray drying this raw material liquid.

2. The method for producing a lactulose-containing powder composition according to claim 1, further comprising the step of carrying out a treatment for altering a ratio between protein and chlorine in advance on the materials used for preparing said raw material liquid.

3. The method for producing a lactulose-containing powder composition according to claim 2, wherein said treatment for altering said ratio between protein and chlorine is ultrafiltration.

4. A lactulose-containing powder composition produced using the method for producing a lactulose-containing powder composition according to any one of claims 1 through 3.

5. A feed additive comprising a lactulose-containing powder composition according to claim 4.

* * * * *

UNITED STATES PATENT AND TRADEMARK OFFICE
CERTIFICATE OF CORRECTION

| | |
|---|---|
| PATENT NO. | : 7,037,377 B2 |
| APPLICATION NO. | : 10/516362 |
| DATED | : May 2, 2006 |
| INVENTOR(S) | : Mamoru Tomita et al. |

It is certified that error appears in the above-identified patent and that said Letters Patent is hereby corrected as shown below:

On the Title Page

In the Title, Item [54], replace both instances of "LACTUROSE-CONTAINING" with -- LACTULOSE-CONTAINING --.

In the Specification

In Column 2, line 2, replace "LACTUROSE-CONTAINING" with --LACTULOSE-CONTAINING--.

In Column 2, line 3, replace "LACTUROSE-CONTAINING" with --LACTULOSE-CONTAINING--.

In Column 2, line 63, replace "In other words, The method" with -- In other words, the method --.

In Column 5, line 20, replace "Flow rate: 1.0 m/min." with -- Flow rate: 1.0 ml/min --.

In Column 14, line 6, replace "was varied within a not exceeding" with -- was varied but not exceeding --.

In Column 14, line 36, replace "second group were fed" with -- second group was fed --.

In Column 14, line 39, replace "third group were fed" with -- third group was fed --.

Signed and Sealed this

Twenty-eighth Day of November, 2006

JON W. DUDAS
*Director of the United States Patent and Trademark Office*